(12) United States Patent
Sasaki et al.

(10) Patent No.: US 8,287,480 B2
(45) Date of Patent: Oct. 16, 2012

(54) HEMODIALYSIS APPARATUS

(75) Inventors: Futoshi Sasaki, Hiroshima (JP); Koji Nakamagoe, Hiroshima (JP)

(73) Assignee: JMS Co., Ltd., Hiroshima (JP)

( * ) Notice: Subject to any disclaimer, the term of this patent is extended or adjusted under 35 U.S.C. 154(b) by 394 days.

(21) Appl. No.: 12/666,993

(22) PCT Filed: Jun. 27, 2008

(86) PCT No.: PCT/JP2008/001682
§ 371 (c)(1),
(2), (4) Date: Dec. 28, 2009

(87) PCT Pub. No.: WO2009/004777
PCT Pub. Date: Jan. 8, 2009

(65) Prior Publication Data
US 2010/0191164 A1    Jul. 29, 2010

(30) Foreign Application Priority Data

Jun. 29, 2007  (JP) .................................. 2007-172945

(51) Int. Cl.
*A61M 37/00* (2006.01)
*B01D 21/30* (2006.01)
(52) U.S. Cl. ...................... 604/6.11; 604/5.04; 210/137
(58) Field of Classification Search ........ 604/4.01–6.01, 604/6.07–6.14, 6.16, 174, 175, 164.01–164.04; 210/137
See application file for complete search history.

(56) References Cited

U.S. PATENT DOCUMENTS

| | | | | |
|---|---|---|---|---|
| 5,580,460 A | * | 12/1996 | Polaschegg | 210/646 |
| 6,066,261 A | * | 5/2000 | Spickermann | 210/739 |
| 7,749,184 B2 | * | 7/2010 | Cavalcanti et al. | 604/6.11 |

FOREIGN PATENT DOCUMENTS

| | | |
|---|---|---|
| JP | 1-75440 | 5/1989 |
| JP | 7-75668 | 3/1995 |
| JP | 11-253550 | 9/1999 |
| JP | P2002-095741 A | 4/2002 |
| JP | P2003-180823 A | 7/2003 |
| JP | P2004-187990 A | 7/2004 |
| JP | P2005-218709 A | 8/2005 |

\* cited by examiner

*Primary Examiner* — Philip R Wiest
(74) *Attorney, Agent, or Firm* — Ohlandt, Greeley, Ruggiero & Perle, LLP

(57) ABSTRACT

A hemodialysis apparatus includes a blood processing machine, a blood circuit through which blood led from a patient flows, a blood pump attached to the blood circuit to pump blood, a dialysate circuit, a clamp disposed downstream of the blood pump for the blood circuit to block the blood circuit, a blood pressure sensor for detecting the pressure of a part of the blood circuit between the blood pump and the blocker, and a control unit connected with the blood pump and the blood pressure sensor. The control unit is configured to determine, based on the pressure detected by the blood circuit pressure detector, whether or not the blood circuit has encountered abnormal conditions while the blood circuit blocked by the clamp is filled with liquid by the blood pump (steps SA2, SA3, and SA5).

11 Claims, 5 Drawing Sheets

HEMODIALYSIS APPARATUS

TECHNICAL FIELD

The present invention relates to hemodialysis apparatuses for use in treatments requiring extracorporeal circulation of the blood of patients, such as hemodialysis, continuous hemodiafiltration, etc., and more particularly pertains to the technical field in which abnormal conditions in a circuit through which the blood circulates can be detected before starting the treatment.

BACKGROUND ART

Conventionally, hemodialysis apparatuses for performing treatments requiring extracorporeal circulation of the blood of patients have been used, for example, for patients with renal failure, drug-addicted people, etc. This hemodialysis apparatus includes a blood processing machine for bringing blood into contact with dialysate via a semipermeable membrane to purify the blood, a blood circuit connected to a blood flow path of the blood processing machine, and a dialysate circuit connected to a dialysate flow path of the blood processing machine.

The blood circuit includes an arterial line through which blood is led from a patient to the blood flow path of the blood processing machine, a venous line through which blood is led from the blood flow path of the blood processing machine back to the patient, and drip chambers attached to the arterial line and the venous line. The blood circuit further includes a line for medication infusion, etc. On the other hand, the dialysate circuit includes a dialysate supply line for supplying dialysate to the dialysate flow path of the blood processing machine, and a dialysate drain line for draining dialysate from the dialysate flow path of the blood processing machine. Furthermore, the hemodialysis apparatus is connected also with pressure monitor lines for monitoring the internal pressures of the circuits, and other components.

As described above, the hemodialysis apparatus is composed of many components. Extreme care should be taken to connect these components and examine the hemodialysis apparatus. Specifically, since, in particular, the blood circuit is connected to a blood vessel of a patient, abnormal conditions, such as disconnection, may cause the following accidents: air may be drawn into the blood circuit so as to be mixed into the body of the patient; and blood in the blood circuit may leak out so that the patient may experience blood loss.

These accidents must be prevented before they occur. Therefore, when treatment is performed, health care workers have examined a blood circuit for abnormal conditions with the greatest care. This examination has placed great physical and mental stress on the health care workers.

To address the above-mentioned problem, hemodialysis apparatuses described in PATENT DOCUMENTS 1 and 2 can automatically detect abnormal conditions in a blood circuit in order to perform safe treatment while reducing stress on health care workers. A blood circuit of the hemodialysis apparatus of PATENT DOCUMENT 1 is connected with a priming fluid reservoir for use in priming. The priming fluid reservoir is disposed above pressure detectors attached to pressure monitor lines. While an arterial line and lines of a dialysate circuit are interrupted, the pressure difference between the priming fluid reservoir and the pressure detector is detected, thereby detecting abnormal conditions in the blood circuit based on the pressure difference.

In the hemodialysis apparatus of PATENT DOCUMENT 2, a pressure monitor line of a blood circuit is connected with an air pump. While the blood circuit is closed, air is pumped to the blood circuit by the air pump to detect the pressure of the blood circuit, thereby detecting abnormal conditions in the blood circuit based on the detected value.

PATENT DOCUMENT 1: Japanese Patent Publication No. 2005-218709

PATENT DOCUMENT 2: Japanese Patent Publication No. 2002-95741

SUMMARY OF THE INVENTION

Technical Problem

However, since, in the hemodialysis apparatus of PATENT DOCUMENT 1, abnormal conditions in the blood circuit are detected based on the pressure difference between the priming fluid reservoir and the pressure measurement device, the priming fluid reservoir must be disposed at the highest possible level in order to provide sufficient detection sensitivity, and therefore preparation for the hemodialysis apparatus is complicated. Furthermore, since the pressure difference between the priming fluid reservoir and the pressure measurement device is detected, abnormal conditions, such as disconnection, which are caused after priming cannot be detected.

Moreover, since, in the hemodialysis apparatus of PATENT DOCUMENT 2, the air pump that is not directly related to blood processing is provided only in order to detect abnormal conditions, this increases the cost of the hemodialysis apparatus. Furthermore, since air that is compressible fluid is pumped to the blood circuit, the time from the start of the pumping of air to when the pressure of the blood circuit is stabilized so that abnormal conditions can be detected is long. Moreover, with use of the air, the pressure of the blood circuit is more likely to vary according to variations in ambient temperature, and thus inaccurate detection results may be provided. In addition, since air is pumped to the blood circuit, abnormal conditions can be detected only before priming. Even if abnormal conditions are caused in the blood circuit during and after priming, the abnormal conditions cannot be detected.

The present invention has been made in view of the foregoing point, and an object thereof is to accurately detect abnormal conditions in a blood circuit within a short time during and after priming without complicating preparation for a hemodialysis apparatus and increasing the cost of the hemodialysis apparatus, thereby increasing the degree of safety of treatment associated with extracorporeal circulation.

Solution to the Problem

To achieve the above-described object, according to the present invention, a blood circuit is filled with liquid by a blood pump, and abnormal conditions in the blood circuit are detected based on the internal pressure of the blood circuit.

Specifically, a hemodialysis apparatus of a first aspect of the invention includes: a blood processing machine including a blood flow path through which blood of a patient flows and a dialysate flow path through which dialysate flows, where the blood flow path and the dialysate flow path are defined by a semipermeable membrane; a blood circuit for introducing the blood led from the patient into the blood flow path and leading the blood flowing through the blood flow path back to the patient; a blood pump attached to the blood circuit to pump blood; a dialysate circuit for introducing dialysate into the dialysate flow path and leading the dialysate flowing through the dialysate flow path from the dialysate flow path; a blocker disposed downstream of the blood pump for the blood circuit to block the blood circuit; a blood circuit pressure detector for detecting an internal pressure of a part of the blood circuit between the blood pump and the blocker; and a control unit connected with the blood pump and the blood circuit pressure detector. The control unit is configured to determine, based on the pressure detected by the blood circuit pressure detector, whether or not the blood circuit has encountered abnormal conditions while the blood circuit blocked by the blocker is filled with liquid by the blood pump.

With this configuration, while the blood circuit is filled with liquid by the blood pump, the internal pressure of the blood circuit is detected, and accordingly a determination is made whether or not the blood circuit has encountered abnormal conditions. Therefore, abnormal conditions in the blood circuit can be detected without being based on the pressure difference of priming fluid as in the known example and using an air pump that is not related to blood processing. Since the pressure difference of priming fluid is not used, priming fluid does not need to be disposed at the highest possible level. This facilitates preparation, and allows abnormal conditions, such as poor connection, to be detected even while blood fills the blood circuit after priming. Furthermore, since an air pump does not need to be used, this prevents the cost of the hemodialysis apparatus from increasing, and further allows abnormal conditions in the blood circuit to be detected even during priming in which the blood circuit is filled with priming fluid as liquid and even under subsequent conditions where the blood circuit is filled with blood. Furthermore, the pressure of the blood circuit can be detected while the blood circuit has been filled with incompressible fluid, i.e., priming fluid or blood. This reduces the time until the detection as compared with the case where the pressure of the blood circuit is detected while the blood circuit has been filled with air. In addition, the pressure of the blood circuit hardly varies according to variations in ambient temperature. As a result, the pressure can be accurately detected.

According to a second aspect of the invention, in the first aspect of the invention, the control unit may be configured to determine, after priming, whether or not the blood circuit has encountered abnormal conditions.

According to a third aspect of the invention, the hemodialysis apparatus of the first or second aspect of the invention may further include a dialysate circuit pressure detector for detecting an internal pressure of the dialysate circuit. The blood circuit may include a pressure monitor line connected with the blood circuit pressure detector, and the control unit may be configured to determine that the pressure monitor line has encountered abnormal conditions when, after comparison between an amount of increase in the internal pressure of the blood circuit detected by the blood circuit pressure detector and an amount of increase in the internal pressure of the dialysate circuit detected by the dialysate circuit pressure detector, it is detected that the amount of increase in the internal pressure of the blood circuit is at least a predetermined value smaller than the amount of increase in the internal pressure of the dialysate circuit.

With this configuration, the use of the blood circuit pressure detector and the dialysate circuit pressure detector, which are attached to a typical hemodialysis apparatus, allows a detection for determining whether or not the pressure monitor line of the blood circuit has encountered abnormal conditions.

According to a fourth aspect of the invention, in any one of the first through third aspects of the invention, the control unit may be configured to determine that liquid leaks from somewhere in the blood circuit when the pressure detected by the blood circuit pressure detector is equal to or smaller than a predetermined pressure.

With this configuration, the use of the blood circuit pressure detector attached to a typical hemodialysis apparatus allows a detection for determining whether or not liquid leaks from somewhere in the blood circuit.

According to a fifth aspect of the invention, in the fourth aspect of the invention, the control unit may be configured to increase the internal pressure of the blood circuit to a higher pressure than the internal pressure of the blood circuit during blood processing and then determine whether or not liquid leaks from somewhere in the blood circuit.

With this configuration, while the internal pressure of the blood circuit is increased to a higher pressure than that during the processing of the patient's blood, it is detected whether or not liquid leaks from somewhere in the blood circuit. In this manner, when one or more of the lines of the blood circuit are loosely connected to the blood circuit so that the amount of leakage of liquid is extremely small, and poor connection is hardly found under low pressures, such as the pressure of the blood circuit during blood processing, these conditions can be found.

According to a sixth aspect of the invention, in any one of the first through fifth aspects of the invention, the control unit may be configured to stop the blood pump with the blood circuit filled with liquid, then continuously obtain the internal pressure of the blood circuit using the blood circuit pressure detector, and determine that the liquid leaks from somewhere in the blood circuit when the blood circuit pressure detector detects that the pressure of the blood circuit has decreased by a predetermined value or more within a predetermined time.

With this configuration, since the internal pressure of the blood circuit is continuously obtained, it can be immediately detected that liquid has leaked from the blood circuit.

According to a seventh aspect of the invention, in any one of the first through sixth aspects of the invention, the dialysate circuit may be blocked.

With this configuration, blockage of the dialysate circuit makes it difficult for liquid filling the blood circuit to flow through the semipermeable membrane of the blood processing machine toward the dialysate circuit when the internal pressure of the blood circuit is to be detected. This can prevent a determination as to whether or not the blood circuit has encountered abnormal conditions from being adversely affected.

According to an eighth aspect of the invention, in any one of the first through seventh aspects of the invention, the blood circuit may include an arterial line for introducing the blood led from the patient into the blood flow path of the blood processing machine, and a venous line for leading the blood flowing through the blood flow path back to the patient. The arterial line and the venous line may be provided with two blood circuit pressure detectors, respectively. The control unit may be connected with the two blood circuit pressure detectors.

With this configuration, when one of the blood circuit pressure detectors is broken down, the other one thereof can be utilized to determine whether or not the blood circuit has encountered abnormal conditions.

According to a ninth aspect of the invention, in any one of the first and third through eighth aspects of the invention, the dialysate circuit pressure detector for detecting the internal pressure of the dialysate circuit may be connected to the control unit, and the control unit may be configured to determine, based on the pressure detected by the dialysate circuit pressure detector, whether or not the blood circuit has encountered abnormal conditions.

Specifically, liquid can move between the blood circuit and the dialysate circuit via the semipermeable membrane of the blood processing machine. Therefore, when the blood circuit pressure detector is broken down, the dialysate circuit pressure detector can be utilized to determine whether or not the blood circuit has encountered abnormal conditions.

Advantages of the Invention

According to the first aspect of the invention, while the blood circuit blocked by the blocker is filled with liquid by the blood pump, a determination is made, based on the pressure detected by the blood circuit pressure detector, whether or not the blood circuit has encountered abnormal conditions. In view of the above, abnormal conditions in the blood circuit can be accurately detected within a short time even during or after priming without complicating preparation and increasing the cost of the hemodialysis apparatus, thereby increasing the degree of safety of treatment.

According to the second aspect of the invention, the determination can be made, after priming, whether or not the blood circuit has encountered abnormal conditions. Therefore, abnormal conditions in the blood circuit can be reliably detected before the initiation of dialysis.

According to the third aspect of the invention, the use of the blood circuit pressure detector and the dialysate circuit pressure detector, which are attached to a typical hemodialysis apparatus, allows a determination as to whether or not the pressure monitor line of the blood circuit has encountered abnormal conditions. Therefore, the hemodialysis apparatus can be configured so that a determination can be made whether or not the pressure monitor line has encountered abnormal conditions without complicating the circuit configuration.

According to the fourth aspect of the invention, the use of the blood circuit pressure detector attached to a typical hemodialysis apparatus allows a determination as to whether or not liquid leaks from somewhere in the blood circuit. Therefore, the hemodialysis apparatus can be configured so that a determination can be made whether or not liquid leaks from somewhere in the blood circuit and whether or not the blood circuit is disconnected from the hemodialysis apparatus without complicating the circuit configuration.

According to the fifth aspect of the invention, the pressure of the blood circuit is increased to a higher pressure than that during the processing of the patient's blood, and then a determination is made whether or not liquid leaks from somewhere in the blood circuit. Therefore, even when the amount of leakage of the liquid is extremely small, the leakage of the liquid can be reliably found before starting the treatment, thereby achieving a safer treatment.

According to the sixth aspect of the invention, the blood pump is stopped while the blood circuit is filled with blood. Thereafter, a determination is made, based on the pressure continuously obtained by the blood circuit pressure detector, whether or not the blood leaks from somewhere in the blood circuit. Therefore, the blood leakage can be immediately detected, thereby addressing the blood leakage promptly.

According to the seventh aspect of the invention, the dialysate circuit can be blocked. This makes it difficult for liquid filling the blood circuit to flow into the dialysate circuit. Thus, a determination as to whether or not the blood circuit has encountered abnormal conditions can be prevented from being adversely affected. Therefore, abnormal conditions in the blood circuit can be accurately detected.

According to the eighth aspect of the invention, the arterial line and the venous line are provided with the blood circuit pressure detectors, respectively, and the control unit is connected with the two blood circuit pressure detectors. Therefore, even when one of the blood circuit pressure detectors is broken down, a determination can be made whether or not the blood circuit has encountered abnormal conditions.

According to the ninth aspect of the invention, the dialysate circuit pressure detector is connected to the control unit, and a determination is made, based on the pressure detected by the dialysate circuit pressure detector, whether or not the blood circuit has encountered abnormal conditions. Therefore, even when the blood circuit pressure detector is broken down, a determination can be made whether or not the blood circuit has encountered abnormal conditions.

DESCRIPTION OF REFERENCE CHARACTERS

1 Hemodialysis Apparatus
4 Control Unit
10 Blood Processing Machine
11 Blood Circuit
12 Dialysate Circuit
13 Blood Pump
21 Arterial Line
23 Venous Line
27 Pressure Monitor Line
33 Clamp (Blocker)
35 Blood Pressure Sensor (Blood Circuit Pressure Detector)
36 Clamp (Blocker)
43 Dialysate Pressure Sensor (Dialysate Circuit Pressure Detector)

DESCRIPTION OF EMBODIMENTS

An embodiment of the present invention will be described in detail below with reference to the drawings. Note that the following description of the preferred embodiment is merely exemplary in nature, and is not intended to limit the scope, applications, and use of the invention.

Figure 1:
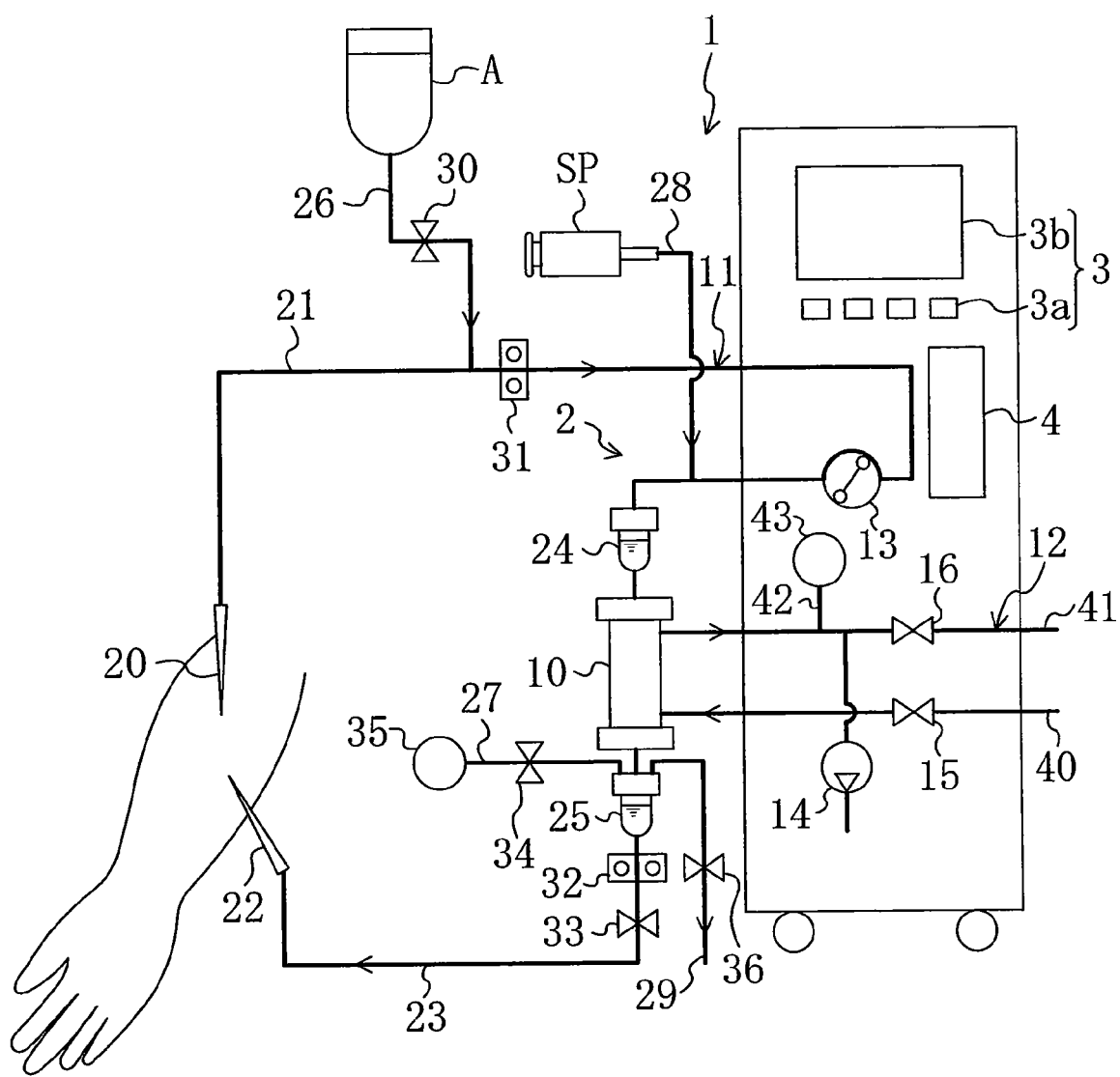
FIG. 1 is a diagram illustrating the usage of a hemodialysis apparatus according to an embodiment.

FIG. 1 is a diagram used to illustrate the case where hemodialysis is performed using a hemodialysis apparatus 1 of the embodiment of the present invention. The hemodialysis apparatus 1 includes a hemodialysis operating unit 2, an operation display unit 3, and a control unit 4. Among them, the hemodialysis operating unit 2 is a unit for actually performing hemodialysis. The control unit 4 is composed mainly of an information processing unit of a computer, and controls the hemodialysis operating unit 2. The operation display unit 3 allows health care workers to enter data, and serves to display various types of information and the entered data.

The hemodialysis operating unit 2 includes a dialyzer (blood processing machine) 10 mainly serving to perform hemodialysis, a blood circuit 11 and a dialysate circuit 12 both connected to the dialyzer 10, a blood pump 13, a water removal pump 14, and on/off valves 15 and 16 for opening and closing the dialysate circuit 12.

The dialyzer 10 is configured so that a cylindrical case contains a plurality of hollow fibers (not illustrated). Although not illustrated, the interiors of these hollow fibers form branches of a blood flow path through which the blood of a patient flows, and a space located outside the follow fibers and in the case form a dialysate flow path through which dialysate flows. In other words, the blood flow path and the dialysate flow path are defined in the dialyzer 10 by semipermeable membranes forming hollow fibers.

Although not illustrated, the case of the dialyzer 10 is formed with a blood inlet port and a blood outlet port both communicating with the interiors of the hollow fibers, and a dialysate inlet port and a dialysate outlet port both communicating with the space located outside the hollow fibers and in the case.

The blood circuit 11 includes an arterial line 21 including a puncture needle 20 used to puncture an artery, a venous line 23 including a puncture needle 22 used to puncture a vein, an arterial drip chamber 24 placed somewhere along the arterial line 21, a venous drip chamber 25 placed somewhere along the venous line 23, a priming line 26 and a syringe pump connection line 28 both branching from the arterial line 21, and a pressure monitor line 27 and an overflow line 29 both connected to the venous drip chamber 25.

The downstream side of the arterial line 21 is connected to the blood inlet port of the dialyzer 10. A blood pump 13 is placed somewhere along the arterial line 21. The blood pump 13 includes an electric motor (not illustrated), and is a so-called squeeze pump configured so that blood is pumped to the venous side of the blood circuit 11 by squeezing a soft tube forming the arterial line 21. The flow rate of the blood flowing through the blood circuit 11 is adjusted by changing the rotational speed of the motor of the blood pump 13. The blood pump 13 is not limited to a squeeze pump, and any other type of pump may be used as the blood pump 13.

The arterial drip chamber 24 is disposed downstream of the blood pump 13. The priming line 26 branches from part of the arterial line 21 located upstream of the blood pump 13, and is connected to a vessel A containing priming fluid. The priming fluid is a physiological salt solution. The priming line 26 is provided with a clamp 30 for opening up and closing off the line 26.

The syringe pump connection line 28 branches from a part of the arterial line 21 between the blood pump 13 and the arterial drip chamber 24, and is connected to a syringe placed in a syringe pump SP. The arterial line 21 is provided with an air bubble sensor 31 for sensing air bubbles in the arterial line 21. The air bubble sensor 31 has conventionally been used for the hemodialysis apparatus 1, and has been known. Therefore, a detailed description of the air bubble sensor 31 is omitted herein.

The upstream side of the venous line 23 is connected to the blood outlet port of the dialyzer 10. A known air bubble sensor 32 for sensing air bubbles in the venous line 23 is disposed downstream of the venous drip chamber 25 of the venous line 23. A clamp 33 for opening up and closing off the venous line 23 is disposed downstream of the air bubble sensor 32 of the line 23. The pressure monitor line 27 is provided with a blood pressure sensor (blood circuit pressure detector) 35 for detecting the internal pressure of the venous line 23. The blood pressure sensor 35 is configured so that the internal pressure of the blood circuit 11 continues to be output at short intervals, e.g., approximately several times a second, and has been known. The pressure monitor line 27 is provided with a clamp 34 for opening up and closing off the line 27.

The overflow line 29 is provided with a clamp 36 for opening up and closing off the line 29. The types and structures of the above-described clamps 30, 33, 34, and 36 are not restrictive. Furthermore, instead of the clamps 30, 33, 34, and 36, forceps or any other tool may be used to open up and close off the lines. Alternatively, the lines may be provided with valve mechanisms so as to be opened up and closed off. The above-described clamps 33 and 36 are blockers of the present invention.

The dialysate circuit 12 includes a supply line 40 connected to a dialysate feeder (not illustrated), a drain line 41, and a pressure monitor line 42. The supply line 40 is connected to the dialysate inlet port of the dialyzer 10. The dialysate is pumped downstream from the upstream side of the supply line 40 by the dialysate feeder. The supply line 40 is provided with the supply line on/off valve 15. Furthermore, the drain line 41 is connected to the dialysate outlet port of the dialyzer 10. The drain line 41 is provided with the drain line on/off valve 16.

The pressure monitor line 42 branches from somewhere along the drain line 41. The pressure monitor line 42 is provided with a dialysate pressure sensor (dialysate circuit pressure detector) 43 for detecting the internal pressure of the drain line 41. The dialysate pressure sensor 43 is configured in the same manner as the blood pressure sensor 35. The drain line 41 is provided with the water removal pump 14. The on/off valves 15 and 16 are composed of electromagnetic valves, etc. When the on/off valves 15 and 16 are both closed, the dialysate circuit 12 is blocked. The pressure monitor line 42 may be attached to the supply line 40.

Figure 2:
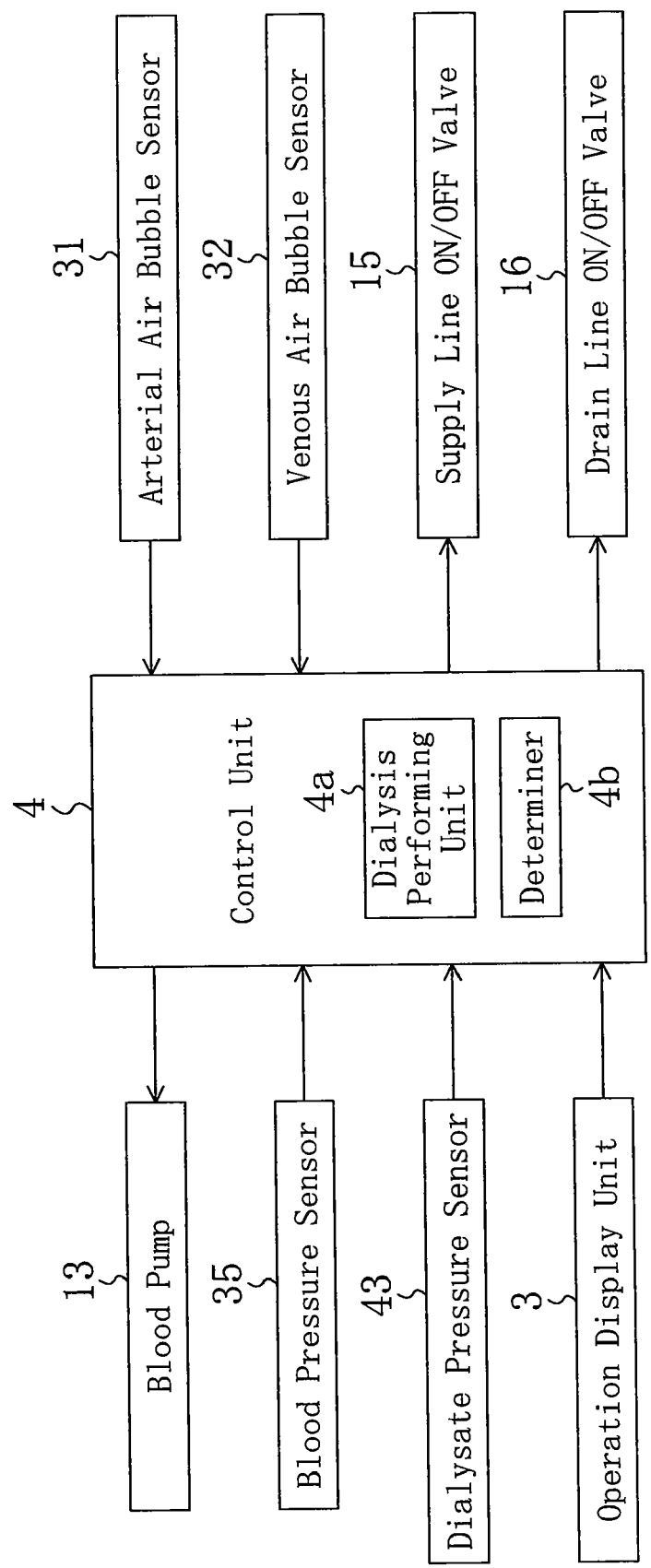
FIG. 2 is a block diagram of the hemodialysis apparatus.

As illustrated in FIG. 2, the blood pump 13, the blood pressure sensor 35, the dialysate pressure sensor 43, the air bubble sensors 31 and 32, the on/off valves 15 and 16, and the operation display unit 3 are connected to the control unit 4. The control unit 4 includes a CPU (central processing unit) (not illustrated), main memory (not illustrated), such as a RAM, and a ROM (not illustrated) in which a control program has been stored. The control unit 4 operates according to the control program.

Operating buttons 3a illustrated in FIG. 1 are used to enter various data on patients and enter performance data of the dialyzer 10, dialysis time, the amount of water removed, etc., for every patient. Furthermore, a display panel 3b is a display composed of a touch panel display. Various data, etc., can be entered by touching operating keys displayed on the display panel 3b. The entered data, the results computed by the CPU, etc., are displayed on the display panel 3b.

As illustrated in FIG. 2, the control unit 4 includes a dialysis performing unit 4a configured so that the blood pump 13 and other components are controlled according to the control program to perform dialysis corresponding to each patient. The configuration of the dialysis performing unit 4a has conventionally been known, and therefore a description thereof is omitted herein. The control unit 4 further includes a determiner 4b for determining whether or not the blood circuit 11 and the blood pump 13 have encountered abnormal conditions.

Figure 3:
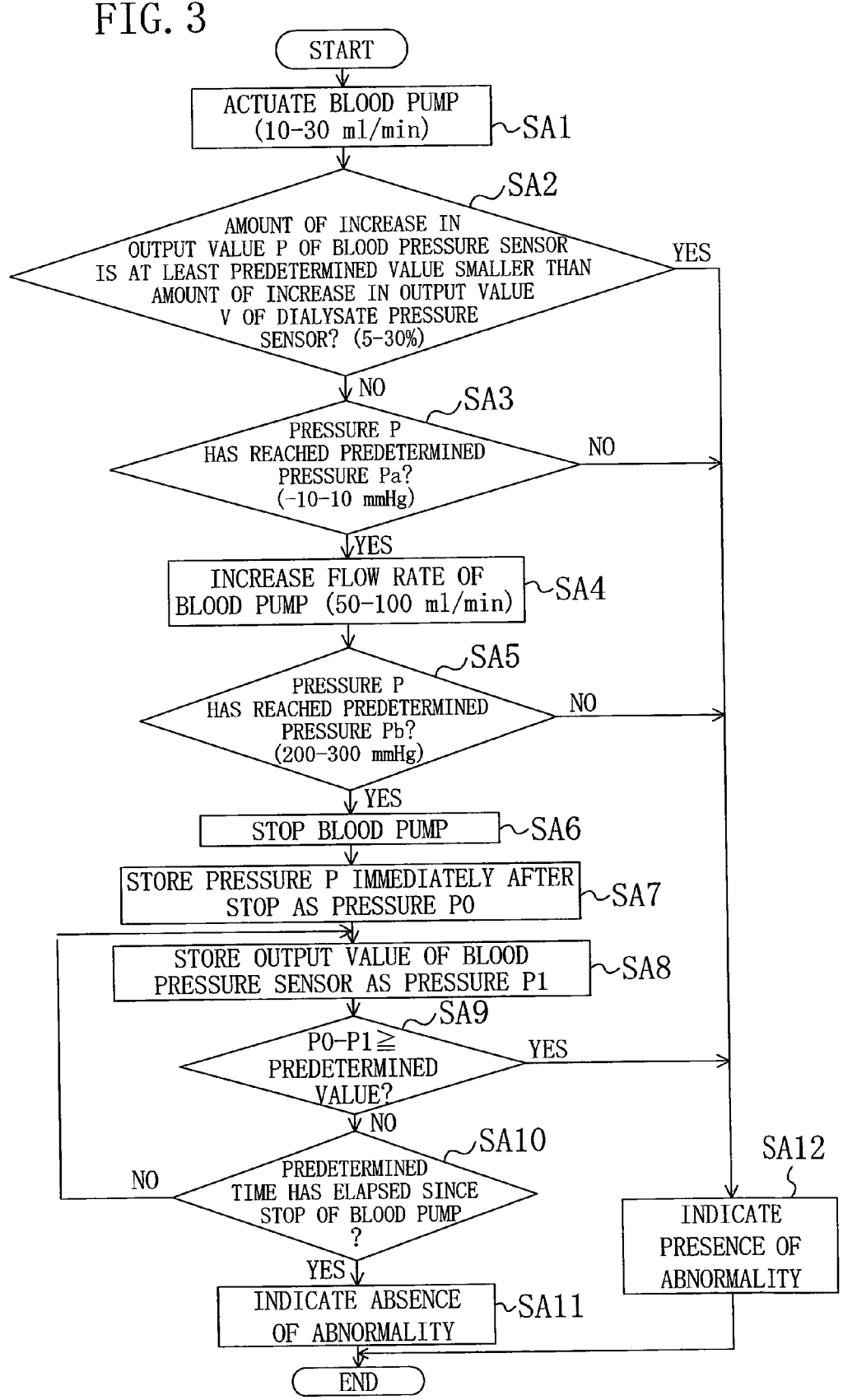
FIG. 3 is a flowchart illustrating a procedure for determining whether or not the blood circuit has encountered abnormal conditions.

The behavior of the determiner 4b will be described hereinafter with reference to the flowchart illustrated in FIG. 3. In step SA1 after start, the blood pump 13 is actuated, thereby filling the blood circuit 11 with liquid. The liquid with which the blood circuit 11 is filled is priming fluid before blood removal, and is blood after blood removal. In this step, the flow rate of the liquid is preferably 10-30 ml/min. Furthermore, the internal pressure of the blood circuit 11 is approximately −50 mmHg before the actuation of the blood pump 13.

In step SA2 following step SA1, a determination is made whether or not the amount of increase in the output value P of the blood pressure sensor 35 (the amount of increase in blood pressure) is at least a predetermined value smaller than the amount of increase in the output value V of the dialysate pressure sensor 43 (the amount of increase in dialysate pressure). This predetermined value is preferably 5-30% of the amount of increase in the output value V of the dialysate pressure sensor 43. In this step SA2, the above-described determination is made within approximately 5-10 seconds.

When the determination in step SA2 is YES, this means that the amount of increase in the output value P of the blood pressure sensor 35 is at least the predetermined value smaller than the amount of increase in the output value V of the dialysate pressure sensor 43. In other words, the pressure monitor line 27 has encountered abnormal conditions where it is blocked or nearly blocked. In this case, the process proceeds to step SA12 to indicate the presence of abnormal conditions. In step SA12, specifically, the message indicating the presence of abnormal conditions may be displayed on the display panel 3b. Alternatively, a pilot lamp (not illustrated) attached to the hemodialysis apparatus 1 may be illuminated or caused to blink. Furthermore, alternatively, a beeper, etc., (not illustrated) attached to the hemodialysis apparatus 1 may sound an audible alarm.

When the determination in step SA2 is NO, this means that the difference between the amount of increase in the output value P of the blood pressure sensor 35 and the amount of increase in the output value V of the dialysate pressure sensor 43 is not great. Therefore, it can be determined that the pressure monitor line 27 has not encountered abnormal conditions.

In step SA3 to which the process proceeds after the determination in step SA2 is NO, a determination is made whether or not the output value P of the blood pressure sensor 35 has reached a predetermined pressure Pa. This predetermined pressure Pa is preferably −10 to 10 mmHg. In step SA3, when the output value P of the blood pressure sensor 35 has reached the predetermined pressure Pa, and therefore the determination is YES, the process proceeds to next step SA4.

On the other hand, when the determination in step SA3 is NO, this means that even with the actuat on of the blood pump 13, the pressure of the blood circuit 11 does not become high enough. In this case, it is likely that the blood circuit 11 will have encountered abnormal conditions. In view of the above, the process proceeds to step SA12 to indicate the presence of abnormal conditions. In this case, the abnormal conditions means the following conditions: one or more of the lines 21, 23, 27, 28, and 29 of the blood circuit 11 are disconnected from the blood circuit 11; the clamp 33 and/or the clamp 36 is not provided; and one or more of the lines 21, 23, 27, 28, and 29 are cracked so that liquid leaks. Although not illustrated, when another line is connected to the dialyzer 10, and other lines are connected to the arterial drip chamber 24 and the venous drip chamber 25, the abnormal conditions also includes disconnection of these lines and a crack in these lines.

In step SA4 to which the process proceeds after the determination in step SA3 is YES, the flow rate of liquid delivered by the blood pump 13 is increased. In this case, the flow rate of this liquid is preferably 50-100 ml/min. In this step SA4, the blood circuit 11 is filled with a preset amount of liquid.

In step SA5 subsequent to step SA4, a determination is made whether or not the output value P of the blood pressure sensor 35 has reached a predetermined pressure Pb. This predetermined pressure Pb is higher than the internal pressure of the blood circuit 11 during usual dialysis. The internal pressure of the blood circuit 11 during usual dialysis is less than 200 mmHg, and accordingly the predetermined pressure Pb is 200 mmHg or more. The upper limit of the predetermined pressure Pb is preferably 300 mmHg or less. The reason for this is that when the upper limit of the pressure Pb is higher than 300 mmHg, this increases the load on the blood circuit 11.

As described above, the presence or absence of abnormal conditions is determined once before the internal pressure of the blood circuit 11 is increased to a higher pressure than that during usual dialysis (step SA3). Therefore, if liquid has leaked, the amount of leakage of the liquid can be reduced.

When the determination in step SA5 is NO, this means that even with the actuation of the blood pump 13, the pressure of the blood circuit 11 does not become high enough. In this case, it is likely that the blood circuit 11 will have encountered the above-described abnormal conditions. In view of the above, the process proceeds to step SA12 to indicate the presence of abnormal conditions.

In step SA6 to which the process proceeds after the determination in step SA5 is YES, the blood pump 13 is stopped.

In step SA7 subsequent to step SA6, the internal pressure of the blood circuit 11 immediately after the shutdown of the blood pump 13 is obtained from the blood pressure sensor 35, and is then stored as the pressure P0.

In next step SA8, the output value of the blood pressure sensor 35 after step SA7 is stored as the pressure P1. Here, the blood pressure sensor 35 outputs the pressure of the blood circuit 11 at short intervals. Therefore, the pressure P1 represents the internal pressure of the blood circuit 11 within a short time, i.e., within one second, after the pressure P0 is obtained by measurement.

In step SA9 subsequent to step SA8, a determination is made whether or not the value derived by subtracting the pressure P1 from the pressure P0 is a predetermined value or more. This predetermined value is preferably 5-10 mmHg.

When the determination in step SA9 is NO, the process proceeds to step SA10. In step SA10, a determination is made whether or not a predetermined time has elapsed after the shutdown of the blood pump 13. This predetermined time is preferably 5-10 seconds. When the determination in step SA10 is NO, the process returns to step SA8. In this step, the value previously stored as the pressure P1 is erased, and the output value P of the blood pressure sensor 35 is again stored as the pressure P1. Thereafter, the process proceeds to step SA9.

When the determination in step SA9 is YES, this means that the internal pressure of the blood circuit 11 has decreased by a predetermined value (5-10 mmHg) or more within a short time (5-10 seconds) after the shutdown of the blood pump 13. In this case, it is likely that liquid in the blood circuit 11 will leak. In view of the above, the process proceeds to step SA12 to indicate the presence of abnormal conditions.

In view of the above, in the above-described steps SA7 through SA10, it can be detected whether or not the pressure of the blood circuit 11 has decreased by the predetermined value or more within the predetermined time after the shutdown of the blood pump 13. In step SA6, when the blood pump 13 is stopped, the pressure of the blood circuit 11 may be smaller than 200 mmHg.

When the determination in step SA10 is YES, this means that the pressure of the blood circuit 11 does not significantly decrease within the short time after the shutdown of the blood pump 13. It is likely that the blood circuit 11 will not have encountered abnormal conditions, such as leakage of liquid from the blood circuit 11. Therefore, the process proceeds to next step SA11 to indicate the absence of abnormal conditions. In step SA11, the message "there is no problem" is preferably displayed on the display panel 3b.

When the air bubble sensors 31 and 32 has sensed air bubbles, the control unit 4 allows the message representing the presence of the sensed air bubbles to be displayed on the display panel 3b, etc., thereby indicating the presence of the sensed air bubbles. Furthermore, since the air bubble sensor 31 is disposed downstream of the priming line 26, the air bubble sensor 31 can also sense, based on an output signal of the air bubble sensor 31, that the priming line 26 has encountered abnormal conditions. The air bubble sensor 31 may be disposed upstream of the priming line 26.

Figure 4:
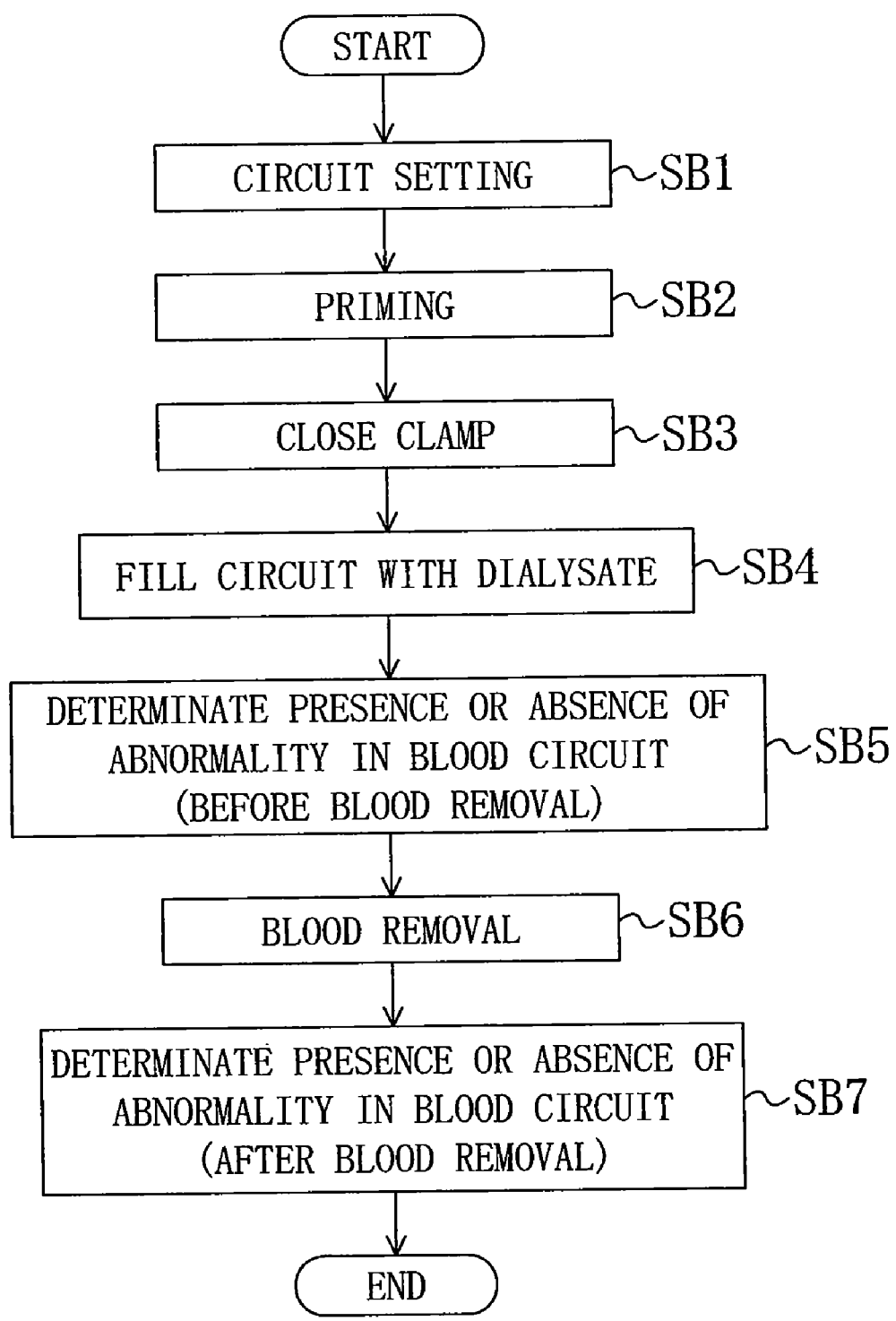
FIG. 4 is a flowchart illustrating a procedure for dialysis preparation.

Next, use of the hemodialysis apparatus 1 configured as described above will be described. Health care workers prepare for dialysis before the initiation of dialysis. The flowchart in FIG. 4 illustrates the procedure of this dialysis preparation. In step SB1 after start, circuits are set up. Specifically, an arterial line 21 and a venous line 23 are connected to a dialyzer 10, and a vessel A for priming fluid and a syringe pump SP are connected to the arterial line 21. Furthermore, a dialysate circuit 12 is connected to the dialyzer 10. Moreover, pressure monitor lines 27 and 42 are connected to a blood pressure sensor 35 and a dialysate pressure sensor 43, respectively. A syringe filled with coagulant, etc., is placed in the syringe pump SP.

In step SB2 subsequent to step SB1, priming is performed. Specifically, a clamp 30 for a priming line 26 is opened, and thus the priming fluid in the vessel A for priming is allowed to flow through a blood circuit 11. In this case, the flow rate of the priming fluid is preferably approximately 150 ml/min. In the above-mentioned manner, the blood circuit 11 and the dialyzer 10 are cleaned, and air bubbles are removed from the interior of the blood circuit 11 and the interior of the blood flow path of the dialyzer 10. In this air bubble removal, the dialyzer 10, etc., is tapped. After the interior of the blood circuit 11 and the interior of the dialyzer 10 are sufficiently cleaned (after priming), a physiological salt solution with which the blood circuit 11 and the dialyzer 10 are to be filled flows through the priming line 26 into the blood circuit 11 and the dialyzer 10, and thus fills the blood circuit 11 and the dialyzer 10.

In step SB3 subsequent to step SB2, a clamp 36 for an overflow line 29 is closed, and an opened clamp 33 is attached to the venous line 23. Thereafter, the process proceeds to step SB4. In step SB4, the dialysate flow path of the dialyzer 10 and the dialysate circuit 12 is filled with dialysate. Then, the on/off valves 15 and 16 of the dialysate circuit 12 is closed, thereby blocking the dialysate circuit 12.

In step SB5 subsequent to step SB4, a determination is made whether or not the blood circuit 11 has encountered abnormal conditions. In this step SB5, control is performed based on the determination procedure illustrated in FIG. 3.

Specifically, after the actuation of the blood pump 13, first, in step SA2, a determination is made whether or not the amount of increase in the pressure of the blood circuit 11 is at least a predetermined value smaller than the amount of increase in the pressure of the dialysate circuit 12. When the difference between the amount of increase in the pressure of the blood circuit 11 and the amount of increase in the pressure of the dialysate circuit 12 is small, the process proceeds to step SA3. In step SA3, a determination is made whether or not the output value P has reached the predetermined pressure Pa. When the output value P has reached the predetermined pressure Pa, the process proceeds to step SA4. In step SA4, the flow rate of the physiological salt solution delivered by the blood pump 13 is increased. Then, the process proceeds to step SA5. In step SA5, a determination is made whether or not the output value P has reached the predetermined pressure Pb. When the output value P has reached the predetermined pressure Pb, the process proceeds to step SA6. In step SA6, the blood pump 13 is stopped. Then, in steps SA7 through SA10, a determination is made whether or not the internal pressure of the blood circuit 11 has significantly decreased within a short time after the shutdown of the blood pump 13. When it is determined that the internal pressure of the blood circuit 11 has not significantly decreased, the absence of abnormal conditions is indicated in step SA11.

On the other hand, when the determination in step SA2 is YES, for example, the pressure monitor line 27 has encountered abnormal conditions where it is blocked or nearly blocked. In this case, the process proceeds to step SA12 to inform an associated health care worker of the presence of abnormal conditions. When the determination in step SA3 is NO even after the determination in step SA2 is NO, this means that the pressure of the blood circuit 11 has not increased. Therefore, the lines 21, 22, and 26-29 of the blood circuit 11 may be disconnected from the blood circuit 11. Alternatively, a physiological salt solution may leak from somewhere in the lines 21, 22, and 26-29, and the dialyzer 10. In this case, the process proceeds to step SA12 to inform an associated health care worker of the presence of abnormal conditions. In this step SA3, it can be also detected that the clamps 33 and 36 are opened.

When the determination in step SA5 is NO even after the determination in step SA3 is YES, this means that the pressure of the blood circuit 11 has not reached the predetermined pressure Pb. Therefore, the lines 21, 22, and 26-29 of the blood circuit 11 may be disconnected from the blood circuit 11. Alternatively, a physiological salt solution may leak from somewhere in the lines 21, 22, and 26-29, and the dialyzer 10. In view of the above, an associated health care worker is informed of the presence of abnormal conditions in step SA12.

Furthermore, when, in steps SA7 through SA10 to which the process proceeds after the determination in step SA5 is YES, it is determined that the pressure of the blood circuit 11 has significantly decreased within a short time after the shutdown of the blood pump 13, the physiological salt solution leaks from the blood circuit 11. In this case, the process proceeds to step SA12. In step SA12, an associated health care worker is informed of the leakage of the physiological salt solution.

In the above-described determinations, the pressure of the blood circuit 11 is increased to a higher pressure than that during usual dialysis. Therefore, when one or more of the lines of the blood circuit 11 are loosely connected to the blood circuit 11, and poor connection is hardly found under low pressures, such as the pressure of the blood circuit 11 during dialysis, these conditions can be found. Furthermore, since the upper limit of the pressure of the blood circuit 11 is 300 mmHg or less, this can prevent an impossible load from being imposed on the blood circuit 11.

As described above, with use of the hemodialysis apparatus 1, while the blood circuit 11 is filled with a physiological salt solution by the blood pump 13 after priming, a determination can be made, based on the output value P of the blood pressure sensor 35, whether or not the blood circuit 11 has encountered abnormal conditions.

Then, the process proceeds to step SB6 in the flowchart illustrated in FIG. 4. In step SB6, blood is removed. Before the blood removal, dialysate is heated to its reference temperature. Then, puncture needles 20 and 22 are inserted into the patient, the blood pump 13 is then actuated, and the clamp 36 for the overflow line 29 is opened, thereby allowing the blood of the patient to flow through the arterial line 21 and an arterial drip chamber 24 into the dialyzer 10. The rotational speed of the blood pump 13 is determined so that the flow rate of the blood is 10-30 ml/min. The physiological salt solution in the blood circuit 11 and the dialyzer 10 flows out of the overflow line 29 until the blood reaches the dialyzer 10. At this time, the clamp 30 for the priming line 26 is closed.

After termination of the blood removal, the clamp 36 for the overflow line 29 is closed, and the clamp 33 for the venous line 23 is also closed. Then, the process proceeds to step SB7. In step SB7, a determination is made whether or not the blood circuit 11 has encountered abnormal conditions as in step SB5. In this step SB7, blood is introduced into the blood circuit 11. The flow rate of the blood is preferably 50-100 ml/min. In this step SB7, a control similar to the control in step SB5 is performed. Therefore, the description of step SB7 is omitted.

In view of the above, according to the hemodialysis apparatus 1 of this embodiment, while the blood circuit 11 is filled with a physiological salt solution or blood by the blood pump 13, a determination is made, based on the output value P of the blood pressure sensor 35, whether or not the blood circuit 11 has encountered abnormal conditions. Therefore, the abnormal conditions of the blood circuit 11 can be detected without being based on the pressure difference of priming fluid as in the known example and using an air pump that is not related to blood processing.

Since the pressure difference of priming fluid is not used as described above, priming fluid does not need to be disposed at the highest possible level. This facilitates preparation, and allows abnormal conditions, such as poor connection, to be detected even while blood fills the blood circuit 11 after priming.

Furthermore, since an air pump does not need to be used, this prevents the cost of the hemodialysis apparatus from increasing, and further allows abnormal conditions to be detected even during priming in which the blood circuit 11 is filled with a physiological salt solution and even after subsequent blood removal in which the blood circuit 11 is filled with blood. Furthermore, while the blood circuit 11 has been filled with incompressible fluid, i.e., a physiological salt solution or blood, the pressure of the blood circuit 11 is detected. This reduces the time until the detection as compared with the case where, while the blood circuit 11 has been filled with air, the pressure of the blood circuit 11 is detected. In addition, the pressure of the blood circuit 11 hardly varies according to variations in ambient temperature. As a result, the pressure can be accurately detected.

In view of the above, abnormal conditions can be accurately detected within a short time even during or after priming without complicating preparation and increasing the cost of the hemodialysis apparatus, thereby increasing the degree of safety of treatment.

The pressure of the blood circuit 11 is increased to a higher pressure than that during dialysis for the patient. Thereafter, when it is detected that the output value of the blood pressure sensor 35 has decreased within a short time, it is determined that liquid has leaked from somewhere in the blood circuit 11. Therefore, the part of the blood circuit 11 from which the liquid may leak can be reliably found before starting the treatment.

Furthermore, the dialysate circuit 12 can be blocked. Therefore, even when the liquid filling the blood circuit 11 has flowed into the dialysate circuit 12, the determination as to whether or not the blood circuit 11 has encountered abnormal conditions can be prevented from being adversely affected. Accordingly, abnormal conditions in the blood circuit 11 can be accurately detected.

Figure 5:
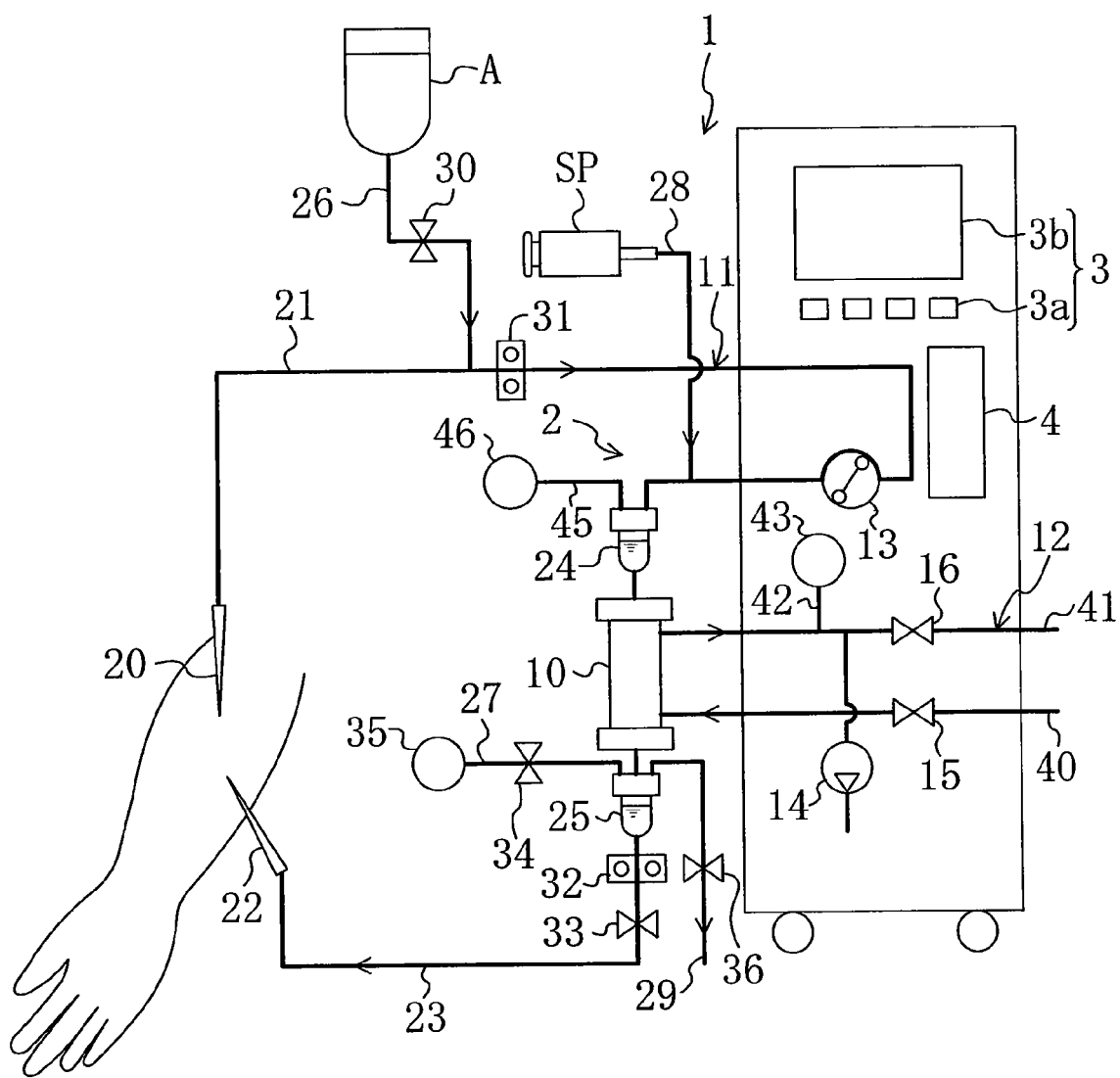
FIG. 5 is a diagram of a modified example corresponding to FIG. 1.

In the above-described embodiment, the pressure monitor line 27 is connected only to the venous line 23 of the blood circuit 11. However, this is not restrictive. As in a first modified example illustrated in FIG. 5, a pressure monitor line 45 may be connected to the arterial drip chamber 24, and the pressure monitor line 45 may be provided with an arterial pressure sensor 46. The arterial pressure sensor 46 is connected to the control unit 4. In this way, for example, when one of the pressure sensors is broken down, or when the pressure monitor line connected with the broken one of the pressure sensors cannot be used, control can be performed based on the output value of the other pressure sensor.

A determination may be made, based on the output value of the dialysate pressure sensor 43, whether or not a part of the blood circuit 11 is defective. Specifically, a pressure from the blood pump 13 acts on the interior of the blood flow path of the dialyzer 10. Therefore, when a physiological salt solution exists in the blood flow path, the physiological salt solution passes through the semipermeable membranes, and flows into the dialysate flow path, resulting in an increase in the output value V of the dialysate pressure sensor 43. By utilizing this mechanism, control can be performed based on the output value of the dialysate pressure sensor 43 when the blood pressure sensor 35 is broken down, or when the pressure monitor line 27 of the blood circuit 11 cannot be used.

In the above-described embodiment, the syringe pump connection line 28 is connected between the blood pump 13 and the arterial drip chamber 24. However, this is not restrictive. The syringe pump connection line 28 may be connected upstream of the blood pump 13. Alternatively, the syringe pump connection line 28 may be omitted.

Although not illustrated, a closed circulation circuit may be formed of an equalization chamber connected to the upstream end of the supply line 40 and the downstream end of the drain line 41, and fluid delivery pumps placed somewhere along the lines 40 and 41. For example, the closed circulation circuit described in Japanese Patent Publication No. 2007-222668 can be utilized as the above-described closed circulation circuit. A flexible diaphragm is disposed in the equalization chamber. The same amount of used dialysate as that of fresh dialysate supplied from one of compartments of the equalization chamber to the supply line 40 is returned through the drain line 41 to the other one of the compartments of the equalization chamber.

The present invention can also be applied to an apparatus for performing, e.g., continuous hemodiafiltration.

Industrial Applicability

As described above, the hemodialysis apparatus of the present invention is suitable when abnormal conditions in a blood circuit need to be detected.

The invention claimed is:

1. A hemodialysis apparatus comprising:
    a blood processing machine including a blood flow path through which blood of a patient flows and a dialysate flow path through which dialysate flows, where the blood flow path and the dialysate flow path are defined by a semipermeable membrane;
    a blood circuit for introducing the blood led from the patient into the blood flow path and leading the blood flowing through the blood flow path back to the patient;
    a blood pump attached to the blood circuit to pump blood;
    a dialysate circuit for introducing dialysate into the dialysate flow path and leading the dialysate flowing through the dialysate flow path from the dialysate flow path;

a blocker disposed downstream of the blood pump for the blood circuit to block the blood circuit;

a blood circuit pressure detector for detecting an internal pressure of a part of the blood circuit between the blood pump and the blocker; and a control unit connected with the blood pump and the blood circuit pressure detector, wherein the control unit is configured to determine, based on the pressure detected by the blood circuit pressure detector, whether or not the blood circuit has encountered abnormal conditions while the blood circuit blocked by the blocker is filled with liquid by the blood pump; and wherein if the pressure detected by the blood circuit pressure detector has not reached a first predetermined level, a first determination is made that an abnormal condition has been encountered; and if the pressure has reached the first predetermined level, flow rate of the blood pump is increased;

when the flow rate of the blood pump is increased, a second determination is made as to whether the pressure has reached a second predetermined pressure; and if the second predetermined pressure has not been reached, a third determination is made that an abnormal condition has been encountered, and if the second predetermined pressure has been reached, the blood pump is stopped.

2. The hemodialysis apparatus of claim 1, wherein the control unit is configured to determine, after priming, whether or not the blood circuit has encountered abnormal conditions.

3. The hemodialysis apparatus of claim 1 further comprising a dialysate circuit pressure detector for detecting an internal pressure of the dialysate circuit, wherein the blood circuit includes a pressure monitor line connected with the blood circuit pressure detector, and the control unit is configured to determine that the pressure monitor line has encountered abnormal conditions when, after comparison between an amount of increase in the internal pressure of the blood circuit detected by the blood circuit pressure detector and an amount of increase in the internal pressure of the dialysate circuit detected by the dialysate circuit pressure detector, it is detected that the amount of increase in the internal pressure of the blood circuit is at least a predetermined value smaller than the amount of increase in the internal pressure of the dialysate circuit.

4. The hemodialysis apparatus of claim 1, wherein the control unit is configured to determine that liquid leaks from somewhere in the blood circuit when the pressure detected by the blood circuit pressure detector is equal to or smaller than a predetermined pressure.

5. The hemodialysis apparatus of claim 4, wherein the control unit is configured to increase the internal pressure of the blood circuit to a higher pressure than the internal pressure of the blood circuit during blood processing and then determine whether or not liquid leaks from somewhere in the blood circuit.

6. The hemodialysis apparatus of claim 1, wherein the control unit is configured to stop the blood pump with the blood circuit filled with liquid, then continuously obtain the internal pressure of the blood circuit using the blood circuit pressure detector, and determine that the liquid leaks from somewhere in the blood circuit when the blood circuit pressure detector detects that the pressure of the blood circuit has decreased by a predetermined value or more within a predetermined time.

7. The hemodialysis apparatus of claim 1, wherein the dialysate circuit is blocked.

8. The hemodialysis apparatus of claim 1, wherein the blood circuit includes an arterial line for introducing the blood led from the patient into the blood flow path of the blood processing machine, and a venous line for leading the blood flowing through the blood flow path back to the patient, the arterial line and the venous line are provided with two blood circuit pressure detectors, respectively, and the control unit is connected with the two blood circuit pressure detectors.

9. The hemodialysis apparatus of claim 1, wherein the dialysate circuit includes a dialysate circuit pressure detector for detecting the internal pressure of the dialysate circuit is connected to the control unit, and the control unit is configured to determine, based on the pressure detected by the dialysate circuit pressure detector, whether or not the blood circuit has encountered abnormal conditions.

10. The hemodialysis apparatus of claim 1, wherein when a determination is made that an abnormal condition has been encountered, the control unit causes a message indicating presence of the abnormal condition to be provided.

11. The hemodialysis apparatus of claim 1, wherein said second predetermined pressure is greater than said first predetermined pressure.

* * * * *